(12) United States Patent
Boesen (10) Patent No.: US 6,852,084 B1
(45) Date of Patent: Feb. 8, 2005

(54) WIRELESS PHYSIOLOGICAL PRESSURE SENSOR AND TRANSMITTER WITH CAPABILITY OF SHORT RANGE RADIO FREQUENCY TRANSMISSIONS

(76) Inventor: Peter V. Boesen, 4026 Beaver Ave., Des Moines, IA (US) 50310

( * ) Notice: Subject to any disclaimer, the term of this patent is extended or adjusted under 35 U.S.C. 154(b) by 0 days.

(21) Appl. No.: 09/560,205

(22) Filed: Apr. 28, 2000

(51) Int. Cl.⁷ .................................................. A61B 5/02
(52) U.S. Cl. ........................ 600/528; 600/586; 181/131; 381/67
(58) Field of Search ................................. 600/528, 486, 600/488, 561, 586; 181/131; 381/67; 128/903

(56) References Cited

U.S. PATENT DOCUMENTS

| | | | |
|---|---|---|---|
| 3,603,881 A | * | 9/1971 | Thorton ...................... 128/903 |
| 3,815,109 A | | 6/1974 | Carraway et al. |
| 4,150,262 A | | 4/1979 | Ono |
| 4,248,241 A | | 2/1981 | Tacchi |
| 4,334,315 A | | 6/1982 | Ono et al. |
| 4,374,382 A | | 2/1983 | Markowitz |
| 4,528,987 A | | 7/1985 | Slocum |
| 4,588,867 A | | 5/1986 | Konomi |
| 4,635,646 A | | 1/1987 | Gilles et al. |
| 4,654,883 A | | 3/1987 | Iwata |
| 4,672,976 A | | 6/1987 | Kroll ........................... 128/715 |
| 4,723,555 A | | 2/1988 | Shue |
| 4,742,831 A | | 5/1988 | Silvain |
| 4,770,189 A | | 9/1988 | Shyu |
| 4,773,427 A | | 9/1988 | Inoue et al. |
| 4,777,961 A | | 10/1988 | Saltzman ..................... 128/715 |
| 4,791,673 A | | 12/1988 | Schreiber |
| 4,791,933 A | | 12/1988 | Asai et al. |
| 4,792,145 A | * | 12/1988 | Eisenberg et al. ........... 600/528 |
| 4,947,859 A | | 8/1990 | Brewer et al. ............... 128/715 |
| 4,981,139 A | | 1/1991 | Pfohl |
| 5,010,890 A | * | 4/1991 | Pfohl et al. .................. 600/586 |
| 5,035,247 A | | 7/1991 | Heimann ..................... 128/715 |
| 5,052,398 A | | 10/1991 | Gober |
| 5,191,602 A | | 3/1993 | Regen et al. |
| 5,201,007 A | | 4/1993 | Ward et al. |
| 5,280,524 A | | 1/1994 | Norris |
| 5,295,193 A | | 3/1994 | Ono |
| 5,298,692 A | | 3/1994 | Ikeda et al. |
| 5,351,694 A | * | 10/1994 | Davis et al. ................. 600/485 |
| 5,360,005 A | * | 11/1994 | Wilk ............................ 600/437 |
| 5,365,937 A | | 11/1994 | Reeves et al. ............... 128/715 |
| 5,381,798 A | | 1/1995 | Burrows |
| 5,417,222 A | | 5/1995 | Dempsey et al. |
| 5,436,564 A | | 7/1995 | Kreger et al. |
| 5,458,123 A | | 10/1995 | Unger |
| 5,467,775 A | * | 11/1995 | Callahan et al. ............ 600/586 |
| 5,492,129 A | | 2/1996 | Greenberger ............... 128/715 |
| 5,557,681 A | * | 9/1996 | Thomasson ................. 381/67 |

(List continued on next page.)

FOREIGN PATENT DOCUMENTS

| | | |
|---|---|---|
| EP | 0 683 621 A | 11/1995 |
| GB | 2 074 817 A | 11/1981 |
| WO | WO 98/34530 | 8/1998 |

OTHER PUBLICATIONS

Article entitled, "A new level of control for Faster, More Predictable Recovery," by Medical Aspect, as early as 1997.

*Primary Examiner*—Robert L. Nasser
(74) *Attorney, Agent, or Firm*—McKee, Voorhees & Sease, P.L.C.

(57) ABSTRACT

A device and a method of sensing and transmitting physiological pressures and body temperatures are disclosed. The device includes a transducer and a transmitter. The transmitter is adapted to broadcast a signal which is modulated by the output of a transducer. The transmitter is also adapted to limit the power of the output signal. The method includes transducing a physiological parameter and broadcasting a signal which is modulated by the transduced parameter. The power of the output signal is limited so that the signal will attenuate within a predetermined distance.

6 Claims, 7 Drawing Sheets

U.S. PATENT DOCUMENTS

| | | | |
|---|---|---|---|
| 5,579,781 A | 12/1996 | Cooke | |
| 5,634,468 A | 6/1997 | Platt et al. | |
| 5,660,177 A | 8/1997 | Faupel et al. | |
| 5,692,059 A | 11/1997 | Kruger | |
| 5,721,783 A | 2/1998 | Anderson | |
| 5,766,208 A | 6/1998 | McEwan | |
| 5,771,438 A | 6/1998 | Palermo et al. | |
| 5,807,258 A | 9/1998 | Cimochowski et al. | |
| 5,931,792 A * | 8/1999 | Packard et al. | 600/528 |
| 5,933,506 A | 8/1999 | Aoki et al. | |
| 5,987,146 A | 11/1999 | Pluvinage et al. | |
| 6,002,777 A * | 12/1999 | Grasfield et al. | 600/528 |
| 6,021,207 A | 2/2000 | Puthuff et al. | |
| 6,099,486 A * | 8/2000 | Fruscello | 600/586 |
| 6,112,103 A | 8/2000 | Puthuff | |
| 6,181,801 B1 | 1/2001 | Puthuff et al. | |
| 6,210,344 B1 * | 4/2001 | Perin et al. | 600/528 |
| 6,341,229 B1 * | 1/2002 | Akiva | 600/586 |
| 6,396,931 B1 * | 5/2002 | Malilay | 381/67 |
| 6,510,918 B2 * | 1/2003 | Bates | 181/131 |

* cited by examiner

WIRELESS PHYSIOLOGICAL PRESSURE SENSOR AND TRANSMITTER WITH CAPABILITY OF SHORT RANGE RADIO FREQUENCY TRANSMISSIONS

BACKGROUND OF THE INVENTION

A. Field of the Invention

The present invention includes a device for monitoring and wirelessly transmitting a physiological pressure. The device includes a pressure transducer and a transmitter which is in operative communication with the transducer. The transmitter is adapted to broadcast a signal which is modulated by a transduced pressure. The transmitter is also adapted to limit the power of the signal so that the signal attenuates to a negligible value within a predetermined distance from the transmitter. Optionally, the invention may also include a receiver which receives a signal broadcast by the transmitter.

B. Problems in the Art

Physiological pressure transducers are known in the art. For example, both stethoscopes and sphygmomanometers are known. Conventional transducers are utilized by applying the transducer to the patient and contemporaneously listening to the output or reading the output from a display.

Even though pressure transducers are known, there are not any known devices which function together with a transducer to make long term recordings of a transduced pressure, such as heart or lung sounds (pressure waves). It would be desirable to make long term recordings of physiological pressures for a number of different reasons.

First, recordings of sounds/pressures allows for more accurate diagnoses and for the greater use of second opinions. In conventional practice, a doctor will apply a stethoscope to a patient and arrive at a conclusion based on the sounds perceived by the doctor. To receive a second opinion, many times another doctor will be able to apply a stethoscope and hear the same sounds. However, for those sounds which are not repetitive, a second doctor must rely on the first doctor to verbally describe the sound perceived by the first doctor. If the second doctor were able to observe a recording of the sound perceived by the first doctor, a better second opinion could be utilized.

In addition, it is desirable to make long term recordings of physiological sounds and pressures to limit medical malpractice liability. For example, it would be easier for a doctor to prove he complied with the standard of care required for the situation by explaining how the doctor made a decision in light of the sound that was actually heard by the doctor. Rather than having to rely on the doctor's oral representation as to what sound was perceived, a fact finder would have the actual sound in front of it, making for a more reliable truth seeking process. There is a need in the art for a method which allows for long term recordings of physiological pressures.

One possible method of making long term measurements of physiological pressures is to connect a pressure transducer to a display or recording device through wire connections. However, wire connections can create additional hazards. For example, wire connections could lead to the possibility of the transducer being disconnected from the recording device by someone tripping over the connection. In addition, wire connections create additional problems when a patient must be moved quickly from one part of the hospital to another. Either the pressure sensor must be removed from the patient, taking additional time, or the monitor or recording device must be moved along with the patient, also requiring additional time and hospital personnel to move the recording device.

One method of dealing with the problems caused by wire connections is to utilize wireless communications between the stethoscope or other transducer and the display device. However, as wireless devices proliferate, there is an increasing probability that an output from a first device will cause electromagnetic interference with a second device. In those hospital rooms that house multiple patients, there is an even greater likelihood that wireless devices will cause interference. This is of particular concern when the devices that are interfered with control some vital function of a patient, such as a ventilator.

A wireless stethoscope is known in the art. However, none of the known stethoscopes limit electromagnetic interference by limiting the power of an output signal. Prior art wireless stethoscope utilize high power output signals which increases the probability of electromagnetic interference between devices that are in close proximity. In addition to causing potential interference, the use of a high power output signal exposes a patient to higher intensity electromagnetic fields. Exposure to electromagnetic fields has been linked with possible long term health problems. Also, the use of a high power output signal leads to quicker battery discharge when batteries are used to power the wireless stethoscopes. Finally, the use of higher power output signals increase multipath problems.

Therefore, it is a primary objective of the present invention to provide a wireless physiological pressure sensor with a transmitter and receiver having the capability of short range radio frequency transmissions which solves problems and deficiencies in the art.

It is a further object of the present invention to provide a physiological pressure sensing method and device which can communicate a sensed pressure through the use of radio frequency communication.

It is a further object of the present invention to provide a wireless pressure transducer and transmitter which minimizes the possibility of electromagnetic interference.

Yet another object of the present invention is to provide a method and device which minimizes a patient's exposure to electromagnetic fields.

It is a further object of the present invention to provide a device and method which minimize battery drain.

It is a further object of the present invention to provide a device and method which minimizes multipath errors.

These, as well as other objects and features of the present invention, will be apparent from the following detailed description and claims in conjunction with the accompanying drawings.

SUMMARY OF THE INVENTION

The present invention includes a device for monitoring and wirelessly transmitting a physiological pressure. The device includes a pressure transducer and a transmitter which is in operative communication with the transducer. The transmitter is adapted to broadcast a signal which is modulated by a transduced pressure. The transmitter is also adapted to limit the power of the signal so that the signal attenuates within a predetermined distance from the transmitter. Optionally, the invention may also include a receiver which receives a signal broadcast by the transmitter.

The present invention can also include a method of monitoring and transmitting a physiological pressure. The method includes the steps of transducing the pressure and broadcasting a signal which is modulated by the transduced pressure. The method also includes the step of limiting the power of the broadcast signal so that the signal attenuates to a negligible value within a predetermined distance. The method can optionally include additional steps such as receiving the broadcast signal, recovering the pressure/sound from the received signal, and storing the measurement in a digital record.

DETAILED DESCRIPTION OF AN EXEMPLARY EMBODIMENT

The present invention will be described as it applies to its preferred embodiment. It is not intended that the present invention be limited to the described embodiment. It is intended that the invention cover all modifications and alternatives which may be included within the spirit and scope of the invention.

Figure 1:
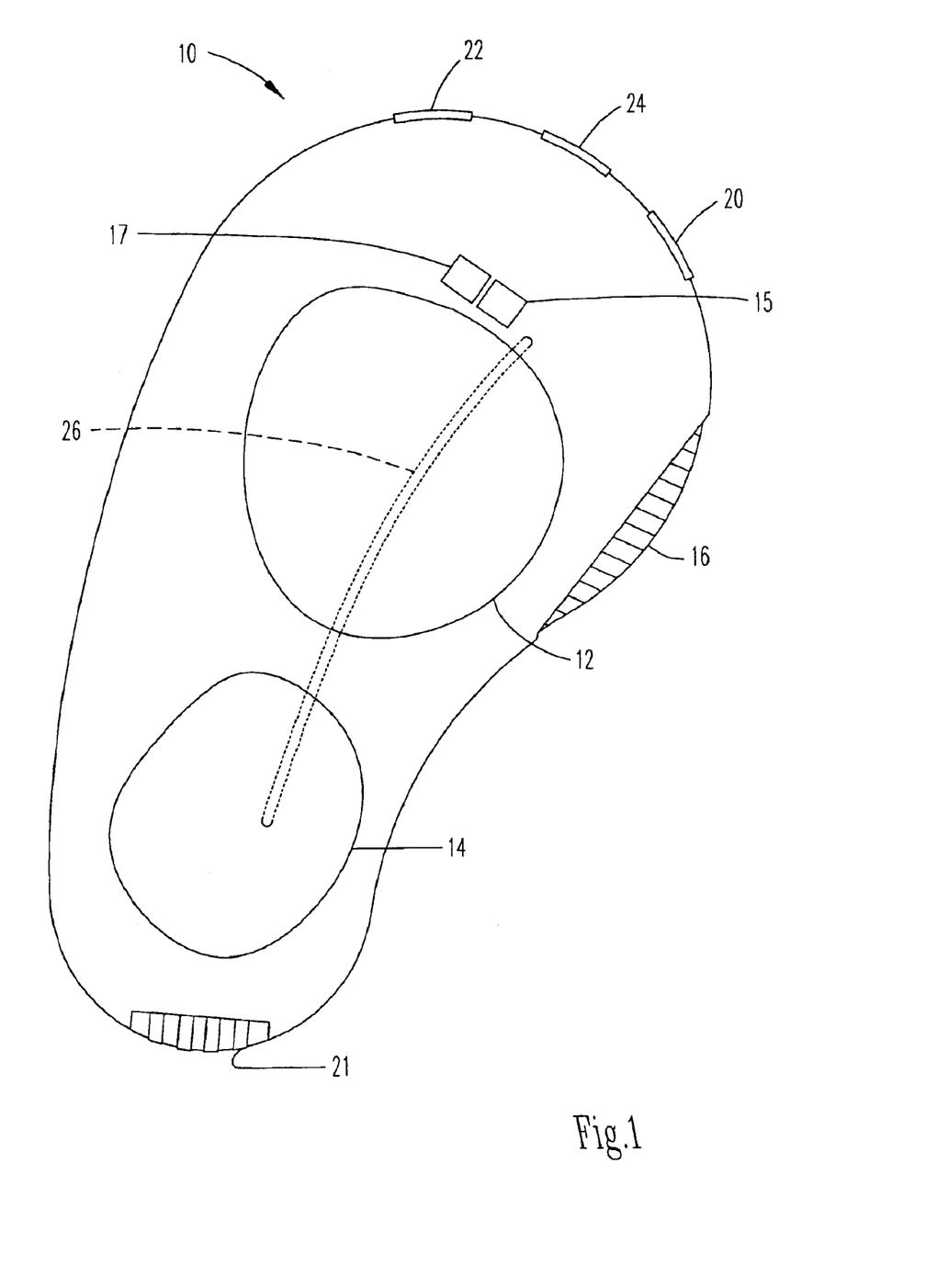
FIG. 1 is a bottom plan view of an embodiment of a wireless stethoscope according to the present invention.

FIG. 1 shows a bottom plan view of a wireless stethoscope 10 according to an embodiment of the present invention. Stethoscope 10 includes a diaphragm 12 and a bell 14. Diaphragm 12 is conventional. Diaphragm 12 is preferably comprised of plastic and operates in conjunction with a microphone to transduce sound waves into electrical signals. Any material which can transduce sound (or other physiological pressure) into an electric or magnetic signal, such as piezoelectric material, could be used. Bell 14 is a conventional stethoscope bell. The sounds can include heart sounds, lung sounds, or bowel sounds.

A temperature sensor 15 and a heart rate sensor 17 may be included. Temperature sensor 15 and heart rate sensor 17 are conventional. A patient's temperature or heart rate may be displayed on LCD 18 (FIG. 2).

Figure 2:
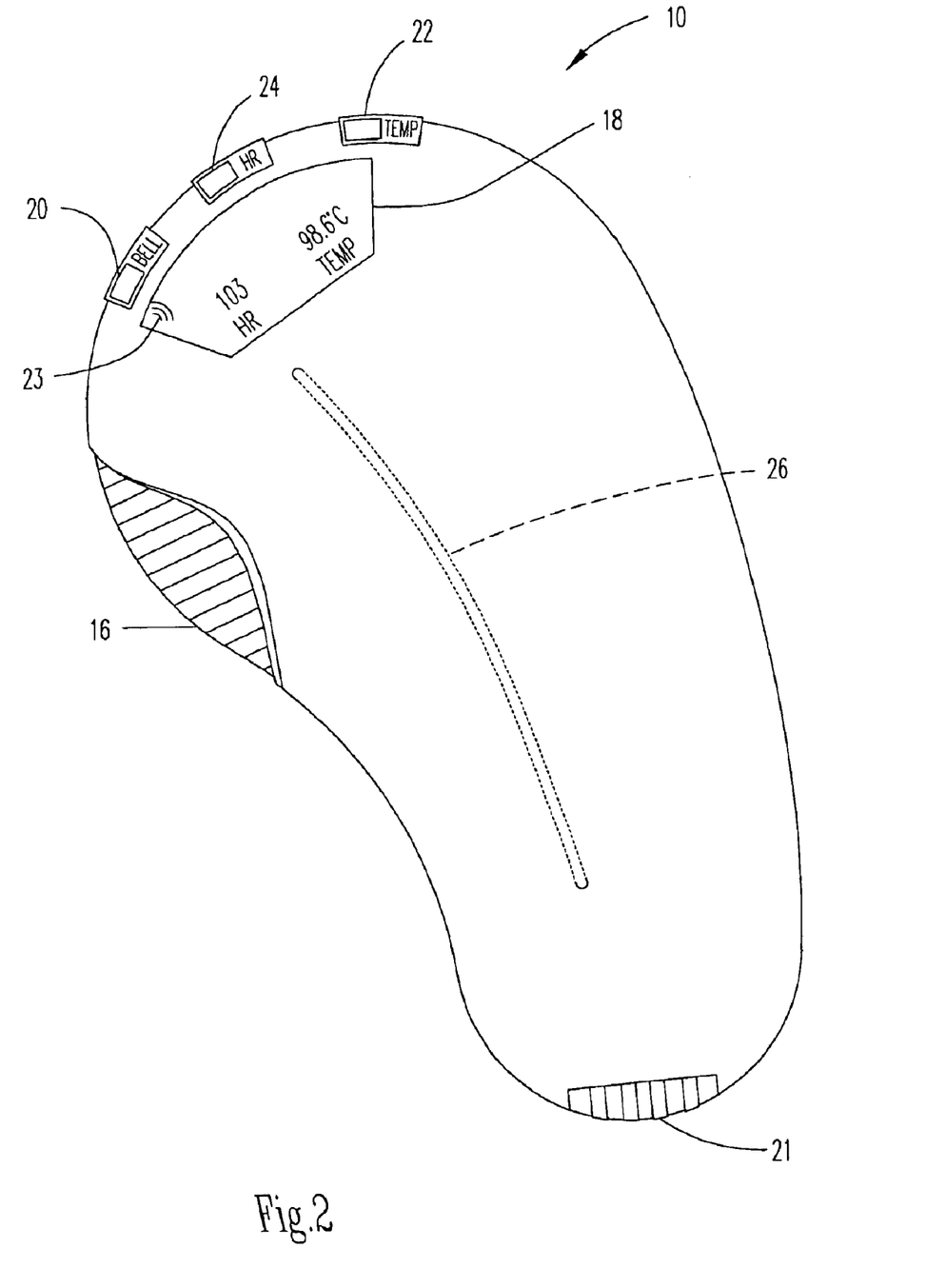
FIG. 2 is a top plan view of the stethoscope of FIG. 1.

FIG. 2 shows a top plan view of stethoscope 10. Stethoscope 10 has a dual detent button 16. A first push or click of button 16 will cause stethoscope 10 to broadcast a signal (explained more fully later on). A second push of button 16 causes stethoscope 10 to record a transduced sound onto a memory chip located inside stethoscope 10. Stethoscope 10 can broadcast a signal while also recording a transduced sound.

A liquid crystal display (LCD) 18 is also included with stethoscope 10. LCD 18 can display patient information, such as a patient's heart rate or temperature. LCD 18 may also have icons to display the operating mode of stethoscope 10, e.g., whether stethoscope 10 is transmitting 23 and/or recording.

Stethoscope 10 includes buttons for the bell 20, the temperature 22, and the heart rate 24. These buttons 20, 22, 24 serve as switches. In the default mode of operation, stethoscope 10 will transmit a signal which is modulated by the output of diaphragm 12. By pushing one of the buttons, the stethoscope 10 will broadcast a signal which is modulated by the output of bell 14, temperature sensor 15, or heart rate sensor 17, depending on which button is selected.

It will be apparent to those skilled in the art that the transmitter could transmit a signal from which any of the sensed parameters (e.g., heart rate or sound) could be recovered. For example, the transmitter could be adapted so that it outputs a digital signal that contains the various sensed parameters at different locations on the signal. The various sensed parameters could then be recovered by a receiver using signal processing techniques that are known in the art. In addition, the transmitter could have a plurality of antennas to transmit different signals corresponding to the sensed parameters. However, for sake of simplicity and cost, the transmitter will usually be designed such that only one parameter or variable is contained in the broadcast signal.

Stethoscope 10 is battery operated. Stethoscope 10 includes a battery recharging port/battery access panel 21. The recharging port 21 is conventional. The cover panel on recharging port 21 can be removed to allow for a change of batteries.

Figure 3:
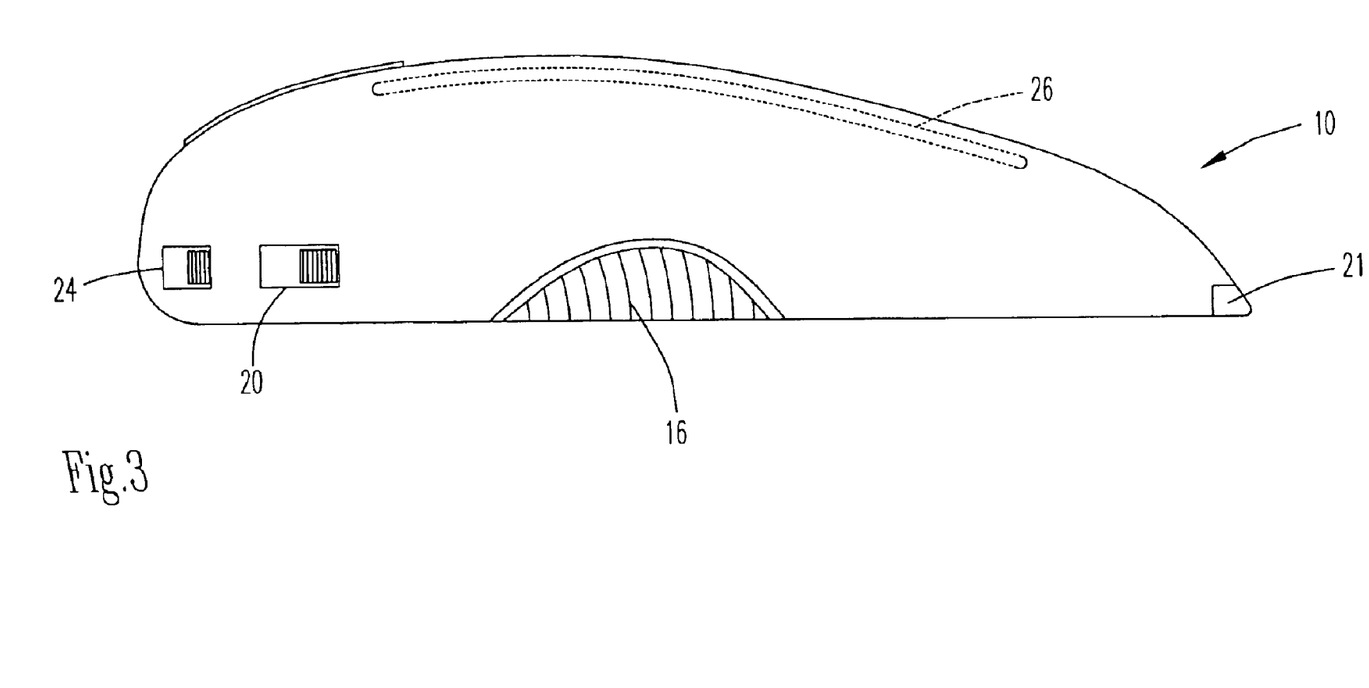
FIG. 3 is a side elevational view of the stethoscope of FIG. 1.

FIG. 3 shows a side view of the wireless stethoscope 10. FIG. 3 shows the antenna 26 in hidden lines. The antenna 26 is housed within stethoscope 10. Of course, the antenna 26 could be external. Antenna 26 is conventional.

Returning to FIG. 1, diaphragm 12 is an operative communication with a transmitter circuit inside stethoscope 10. The transmitter circuit includes an antenna 26. The transmitter circuit is adapted to broadcast a signal which is modulated by the output of diaphragm 12. A receiver can be provided which can recover the sounds from the broadcast signal.

Figure 4:
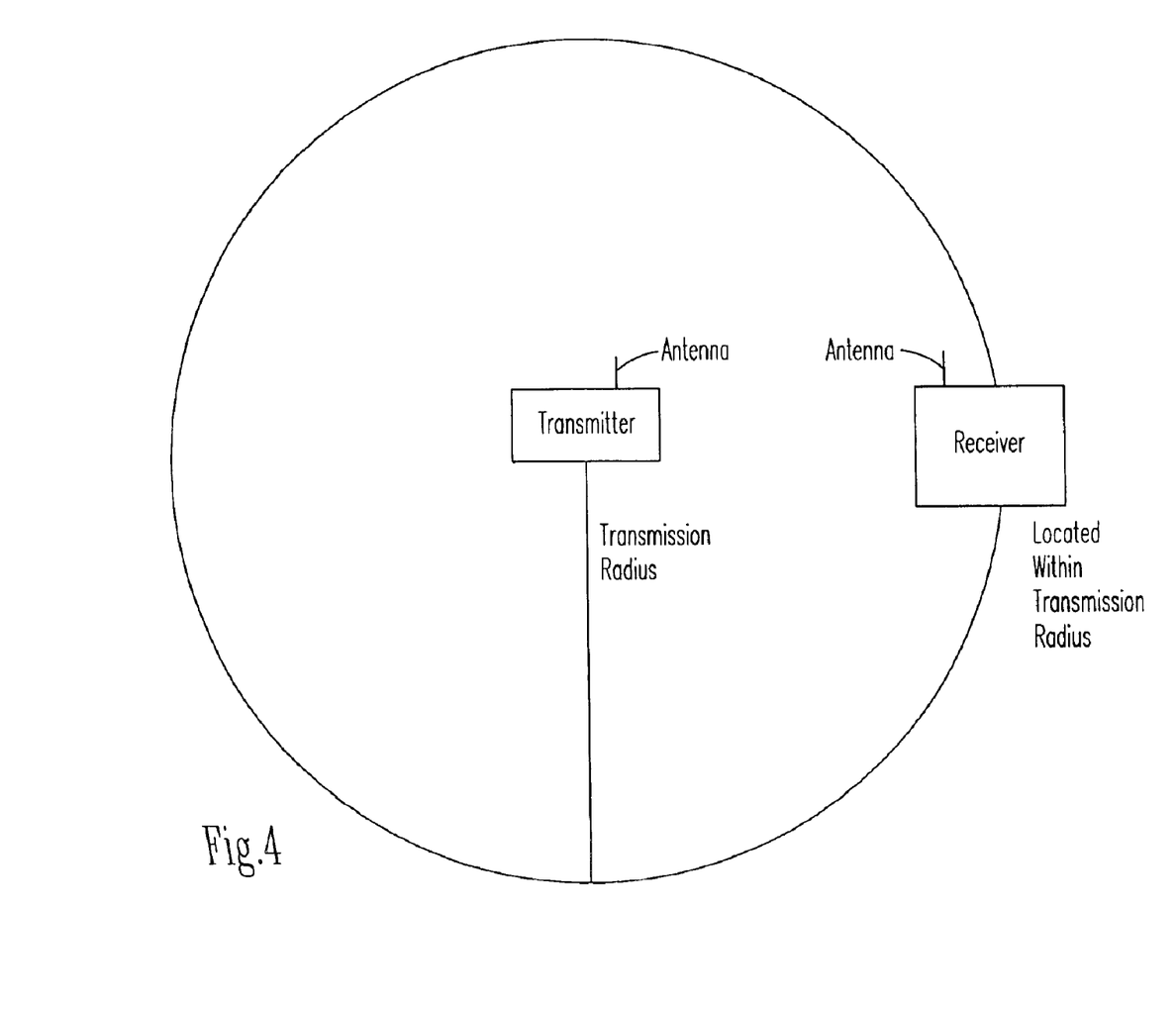
FIG. 4 is a schematic diagram which illustrates the limited range transmission according to an aspect of the present invention.

Preferably, the power of the broadcast signal is limited so that the signal will attenuate to a negligible value within a predetermined distance from the transmitter. As used throughout the present application, signal attenuation refers to the lessening in signal strength to at most a negligible value such that the signal cannot be effectively received by a corresponding or matching receiver. FIG. 4 shows a schematic representation of this scheme. For a hospital setting, the transmission radius is preferably 15 feet or less, with 10 feet being ideal.

The actual power of the broadcast signal will depend on a number of factors, such as the frequency of the signal, the distance in which the signal should attenuate, the temperature and humidity of the environment in which the signal is broadcast, etc. The broadcast signal is preferably a radio frequency signal at about either 900 MHz or 2.4 GHz, as these two frequencies are still open to the public. Preferably, the broadcast signal is a digital spread spectrum signal. It will be apparent to those skilled in the art that there are many ways to generate the broadcast signal, and many different modulation techniques could be utilized.

As noted earlier, selecting one of the switches or buttons 20, 22, 24 (FIG. 2) will place the output of the sensor in operative communication with the transmitter. The output signal of the transmitter will then be modulated by the output of the corresponding sensor.

It should be noted that stethoscope 10 could also include a receiver. There may be times when it is desirable to have stethoscope 10 receive instructions from a remote transmitter. For example, stethoscope 10 could be configured to receive instructions from a computer that is part of a wireless computer network, or from some other transmitter. The computer may transmit instructions to stethoscope to tell stethoscope 10 to perform a function, such as begin transmitting or turn the power off.

By limiting the output power of the broadcast signal, wireless stethoscope 10 will consume less power. For a battery-powered stethoscope, the batteries will have to be recharged or changed less frequently. Also, the intensity of the broadcast signal is smaller, exposing a patient to minimal electromagnetic radiation. Since the broadcast signal attenuates within a predetermined distance from the transmitter, there is a decreased probability that devices outside the transmission radius (FIG. 4) will suffer from electromagnetic interference. In addition, a receiver will not suffer from as many multipath problems because there is less chance that a reflected signal will reach the receiver.

Rather than using a stethoscope as a pressure transducer, a sphygmomanometer could be used. The sphygmomanometer includes a transmitter in operative communication with an output of the sphygmomanometer. The transmitter broadcasts a signal which is modulated by the output of the sphygmomanometer. As previously described, the power of the broadcast signal is limited so that the signal will attenuate within a predetermined distance from the transmitter.

Figure 5:
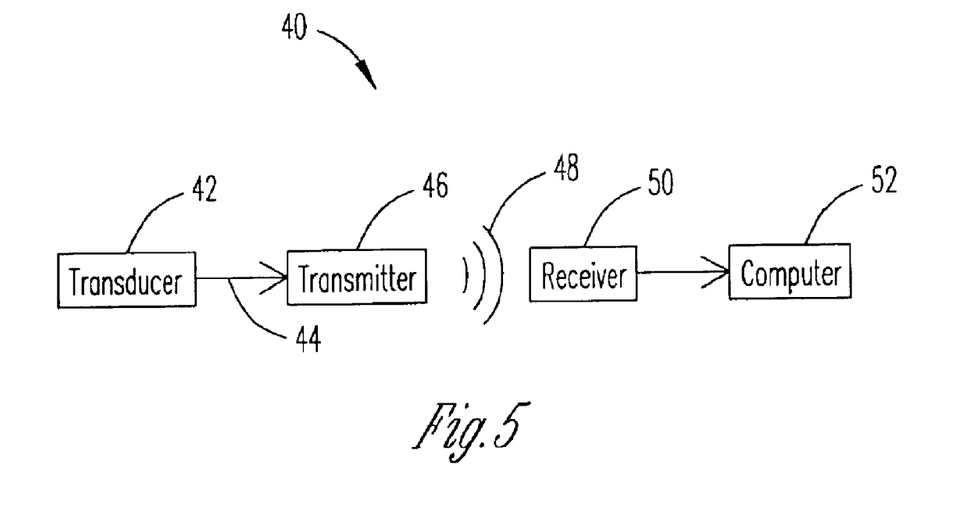
FIG. 5 is a block diagram which illustrates an embodiment of a pressure transducing system according to the present invention.

FIG. 5 shows a block diagram of a pressure transducing system 40 according to the present invention. The system 40 includes a transducer 42 (either a pressure transducer or a thermal transducer). The output 44 of the transducer 42 is input into a transmitter 46. Transmitter 46 broadcasts a signal 48 which is received by the receiver 50. Receiver 50 can be adapted to recover a transduced pressure from the broadcast signal 48, using signal processing techniques that are known in the art.

In addition, receiver 50 could have an analog-to-digital converter which could digitize a recovered pressure. This digitized version could be conveyed to a digital computer 52 or could be written to a digital storage medium, such as a compact disc. Note that with the availability of large scale digital storage mediums, long term recordings of pressures, in excess of 24 hours, could be made. This could be important in proving that there was no indication of imminent danger in those unfortunate cases where a patient dies while being monitored. This may help prevent frivolous medical malpractice litigation.

As noted earlier, there could be a second receiver in operative communication with the transducer 42 or the transmitter 46. For example, computer 52 could have a transmitter and could output signals to a second receiver. The second receiver could in turn "instruct" the transducer 42 or transmitter to perform a function, such as begin transmitting or operate in standby mode.

The physiological pressure sensor and transmitter combination of the present invention is particularly well suited to communicate with a receiver having a bone conduction sensor, an air conduction sensor, or both and also with a transceiver. Such devices are disclosed in co-pending U.S. Ser. No. 09/309,107, filed May 10, 1999, and U.S. Ser. No. 09/416,168, filed Oct. 11, 1999, the disclosures of which are hereby incorporated by reference in their entirety.

Figure 6:
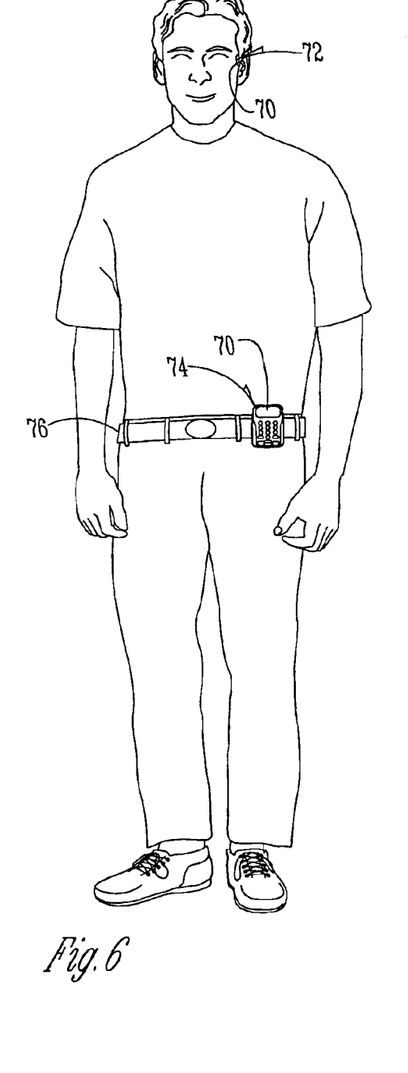
FIG. 6 is a pictorial view showing a user wearing a receiver and transmitter system.

FIG. 6 illustrates a receiver and transmitter system 70 as worn by a user. The user wears the ear piece 72 and the transceiver unit 74. The transceiver unit 74 may be worn on the user's belt 76, though it is also possible to store the transceiver unit 74 in a number of other areas which may be convenient for the user, such as a shirt pocket, coat pocket, or vest pocket.

Figure 7:
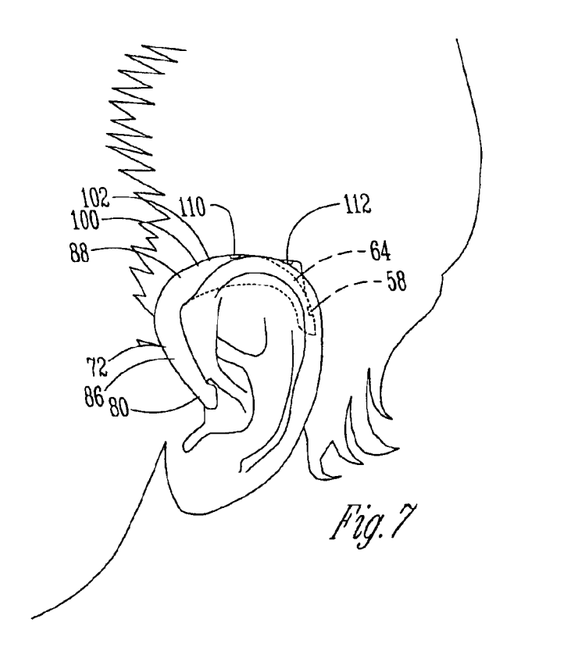
FIG. 7 is a perspective view of the ear piece unit of the receiver and transmitter system of FIG. 6.

As seen in FIG. 1, the ear piece 72 includes an external ear canal portion 80 having a bone conduction sensor 82 in contact with the external auditory canal epithelium of the user, an air conduction sensor or microphone 85, and a speaker 84. A casing 86 is also provided, having an ear attachment portion 88 and a fitting portion 90 that connects the ear attachment portion 88 with the bone conduction sensor 82, the air conduction sensor 85, and speaker 84. The ear attachment portion 88 is contoured to comfortably fit into the angle between the ear auricle and the temporal bone of the skull of the user and is preferably made of a lightweight aluminum or plastic material. It can be appreciated that the primary purpose of the ear attachment portion 88 is to secure the ear piece 72 in proper position. The fitting portion 90 is integral with the ear attachment portion 88 and is reinforced with a flexible wire so that the ear piece 72 may be adapted to fit the user and maintain the bone conduction sensor 82 and the air conduction sensor 85 in their proper positions with the external auditory canal 94 of the user.

Figure 8:
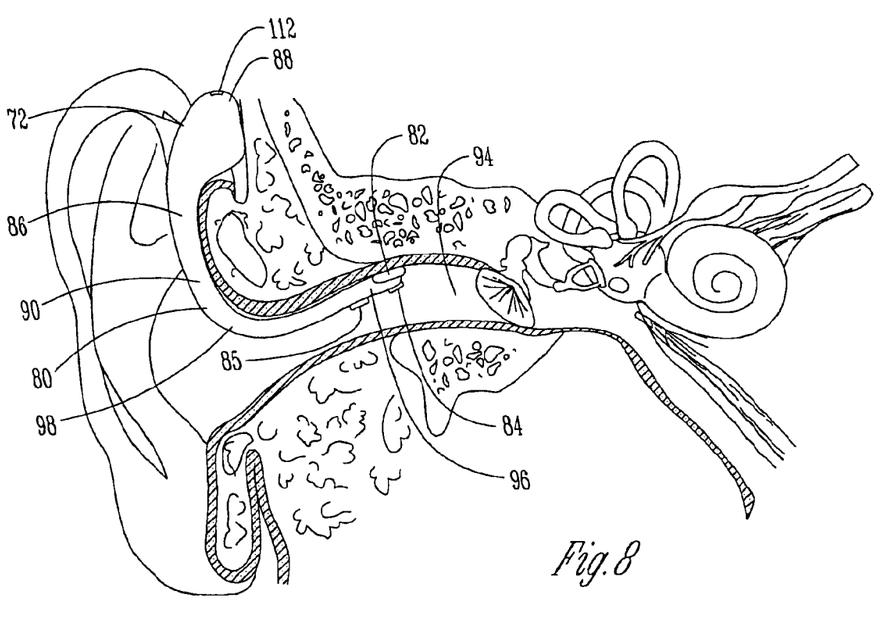
FIG. 8 is a cross-sectional view of the ear piece unit of FIG. 7 taken through the external auditory canal of the user.

As is best shown in FIG. 8, the ear piece 72 should be fit so that the bone conduction sensor 82 is in contact with a portion of the external auditory canal 94 near the bony-cartilaginous junction. It is preferred that the bone conduction sensor 82 rest against the posterior superior wall of the external auditory canal 94, with the flexible wire of the fitting portion 90 shaped to bias the bone conduction sensor 82 into position. Fitting the device and calibrations may be performed by the user or with the assistance of a physician or an audiologist/audiology technician.

The external ear canal portion 80 is formed so that the bone conduction sensor 82 may be inserted into the external auditory canal 94 of the user and nonocclusively contact against the posterior superior wall of the bony canal. The bone conduction sensor 82 is intended to pick up, as the voice signals, the vibrations of the upper wall of the external auditory canal 94 at the time of uttering the voice sounds. When the user utters voice sounds, these sounds reach the mastoid bones. These sound vibrations in the external auditory canal portion in contact with the bone sensor 82 are then processed.

In addition to the bone conduction sensor 82, the external ear canal portion 80 also includes an air conduction sensor or microphone 85. Like the bone conduction sensor 82, the air conduction sensor 85 is of standard construction and may be obtained from various hearing aid manufacturers.

A resilient member 96 is preferably positioned between the air conduction sensor 85 and the bone conduction sensor 82 in such a manner that the external sound collected by the air conduction sensor 85 will not be transmitted to the bone conduction sensor 82. Additionally, the inner ear portion 80 also includes a speaker 84. The speaker 84 is of a type well known in the art and common in the hearing aid industry. The speaker 84 is positioned directly in line with the tympanic membrane to facilitate clear transmissions while maintaining a low power output.

A circuit portion 98 transmits the electrical signals from both the bone conduction sensor 82 and the air conduction sensor 85 to a speech processor 100. The bone conduction sensor 82 and the air conduction sensor 85 are both tuned to receive frequencies within the range of audible human speech, approximately 50 to 8000 Hertz.

The speech processor 100 is of a conventional construction used in many hearing aids and employs a digital processing scheme to package the voice signal for transmission across a wireless linkage. The speech processor 100 will be programmed to extract similarities from air and bone transmission, comparing the similarities in signal and then transmitting via a wireless linkage to a cellular telephone transceiver or other receiving device. The speech processor 100 also filters out through band pass filters 102 sounds outside the frequency of normal human speech.

The speech processor 100 samples a portion of the electrical signals of voice sound information from the air conduction sensor 85 and a portion of the electrical signals of voice sound information from the bone conduction sensor 82. The speech processor 100 then transmits the selected voice signal to an ear piece transceiver 64. The ear piece transceiver 64 is preferably a wireless radio frequency transceiver well known in the art which includes a multi directional antenna 112. The ear piece transceiver 64 sends the voice signal to the transceiver unit 74. The ear piece transceiver 64 also receives incoming signals from the transceiver unit 74 and sends them to the speaker 84.

The transceiver unit 74 includes componentry which is common in the art. The transceiver unit 74 receives the relatively low powered radio frequency (RF) signals from the ear piece transceiver 64 via an RF local area network antenna, processes the signal, and transmits an amplified RF signal. Further, the transceiver unit 74 receives incoming data through a linkage antenna and transmits this to the ear piece transceiver 64 using the low powered RF signals. The transceiver unit 74 may transmit or receive using analog or digital technology.

Note that this system is particularly advantageous when a doctor is wearing the transceiver and transmitter system 70. The doctor could listen to sounds from stethoscope 10 and make contemporaneous observations. These observations could be transmitted by transceiver 74 or transceiver 64 to a computer. Using the voice recognition techniques disclosed in incorporated U.S. Ser. No. 09/309,107, or other voice recognition techniques, the computer could store the observations in a patient-linked database. Further, because signals from transceiver 74 or transceiver 64 and from stethoscope 10 can have their own addresses or identifiers, a computer could receive signals from both at the same time. Thus, both the transduced sound (pressure) and the doctors observations could be recorded together.

A general description of the present invention as well as a preferred embodiment has been set forth above. Those skilled in the art will recognize and be able to practice additional variations in the methods and devices described which fall within the teachings of this invention. Accordingly, all such modifications and additions are deemed to be within the scope of the invention which is to be limited only by the claims appended hereto.

I claim:

1. A new device for monitoring one of a plurality of physiological pressures associated with a patient, the device comprising:
    a housing for protecting the device, the housing having a first planar surface adapted for placement on a patient;
    at least one pressure transducer integral with the housing and adapted for placement on the patient, the at least one pressure transducer providing an output signal;
    a transmitter in operative communication with the at least one pressure transducer, and operatively attached to the housing, the transmitter adapted to broadcast a signal which is modulated by an output of the at least one pressure transducer; and
    a display secured to the housing and operatively connected to the at least one pressure transducer for displaying a representation of the output from the at least one pressure transducer, the display adapted for placement on the patient, a memory disposed within the housing and operatively connected to the at least one pressure transducer for storing an audio representation of the output signal;
    wherein the at least one pressure transducer includes a bell portion and a diaphragm portion disposed along said first surface, and the device includes a switch for selecting either an output of the bell or the diaphragm as the output signal.

2. The device of claim 1 further comprising:
    a receiver which can be tuned to receive a signal from the transmitter.

3. The device of claim 2, further comprising:
    a computer in operative communication with the receiver.

4. The device of claim 1, further comprising:
    a temperature sensor, wherein the switch selects the output of the bell portion, the output of the diaphragm portion, or an output of the temperature sensor as the output signal, and wherein the display is further adapted to display a representation of the output from the temperature sensor.

5. The device of claim 1, further comprising:
    a pulse sensing transducer, wherein the switch selects the output of the bell portion, the output of the diaphragm portion, or an output of the pulse sensing transducer as the output signal, and wherein the display is further adapted to display a representation of the output from the pulse sensing transducer.

6. The device of claim 1 wherein the transmitter is adapted to limit the power of the broadcast signal so that the signal will attenuate to at most a negligible value within a predetermined distance from the transmitter.

* * * * *

UNITED STATES PATENT AND TRADEMARK OFFICE
CERTIFICATE OF CORRECTION

PATENT NO. : 6,852,084 B1
DATED : February 8, 2005
INVENTOR(S) : Boesen, Peter V.

It is certified that error appears in the above-identified patent and that said Letters Patent is hereby corrected as shown below:

Column 8,
Line 2, should read -- 1. A new wireless device for monitoring one of a plurality of --

Signed and Sealed this

Twenty-sixth Day of April, 2005

JON W. DUDAS
*Director of the United States Patent and Trademark Office*